(12) United States Patent
Leiboff et al.

(10) Patent No.: US 7,210,609 B2
(45) Date of Patent: May 1, 2007

(54) STAPLING APPARATUS HAVING A CURVED ANVIL AND DRIVER

(75) Inventors: Arnold R. Leiboff, Stony Brook, NY (US); Joseph Zipper, Miller Place, NY (US); Robert Farrish, Coram, NY (US); Jay Leiboff, Fair Lawn, NJ (US)

(73) Assignee: Tools for Surgery, LLC, Stony Brook, NY (US)

( * ) Notice: Subject to any disclaimer, the term of this patent is extended or adjusted under 35 U.S.C. 154(b) by 0 days.

(21) Appl. No.: 11/193,600

(22) Filed: Jul. 29, 2005

(65) Prior Publication Data

US 2006/0049231 A1 Mar. 9, 2006

Related U.S. Application Data

(60) Provisional application No. 60/592,548, filed on Jul. 30, 2004.

(51) Int. Cl.
*A61B 17/04* (2006.01)
*A61B 17/068* (2006.01)
*A61B 17/00* (2006.01)

(52) U.S. Cl. .............. 227/180.1; 227/176; 227/181.1; 227/19

(58) Field of Classification Search ............. 227/180.1, 227/19, 179.1, 176.1, 178.1
See application file for complete search history.

(56) References Cited

U.S. PATENT DOCUMENTS 3,080,564 A 3/1963 Strekopitov et al.
3,269,630 A 8/1966 Fleischer
3,275,211 A 9/1966 Hirsch et al.
3,315,863 A 4/1967 O'Dea
3,472,231 A 10/1969 Neibel et al.

(Continued)

FOREIGN PATENT DOCUMENTS

WO WO 02/09595 A1 2/2002

(Continued)

OTHER PUBLICATIONS

Abstract of Subtotal colectomy vs. intraoperative colonic irritation in the management of obstructed left colon carcinoma. Torralba JA, Robles R, Parrilla P. Lujan JA, Liron R, Pinero A., Feman JA. Dis Colon Rectum. Jan. 1998;41(1):18-22.

(Continued)

*Primary Examiner*—Brian Nash
(74) *Attorney, Agent, or Firm*—Brian Roffe

(57) ABSTRACT

Stapler, in particular for hemorrhoidal use, includes a body, an elongate, fixed jaw part connected to the body and including a curved anvil defining staple-forming pockets and a curved portion defining an opening bound on lateral and longitudinal sides, an actuating jaw part including a curved staple driver and optionally a cutting knife, a trigger coupled to the body for actuating the actuating jaw part and an adjustment mechanism for moving the actuating jaw part to vary a longitudinal dimension of the opening defined between a staple cartridge and the anvil. When the actuating jaw part is actuated by the trigger, the staple driver forces staple blanks in the staple cartridge into staple-forming pockets of the anvil to form staples in tissue retained in the opening, while the cutting knife, when present, amputates the tissue.

20 Claims, 5 Drawing Sheets

U.S. PATENT DOCUMENTS

| | | |
|---|---|---|
| 3,494,533 A | 2/1970 | Green et al. |
| 3,589,589 A | 6/1971 | Akopov |
| 3,692,224 A | 9/1972 | Astafiev et al. |
| 3,935,981 A | 2/1976 | Akopov et al. |
| 3,949,923 A | 4/1976 | Akopov et al. |
| 4,296,881 A | 10/1981 | Lee |
| 4,508,253 A | 4/1985 | Green |
| 4,527,724 A | 7/1985 | Chow et al. |
| 4,530,453 A | 7/1985 | Green |
| 4,566,620 A | 1/1986 | Green et al. |
| D284,097 S | 6/1986 | Green |
| D284,098 S | 6/1986 | Green |
| D284,403 S | 6/1986 | Green |
| 4,605,004 A | 8/1986 | Di Giovanni et al. |
| 4,606,344 A | 8/1986 | Giovanni |
| D285,604 S | 9/1986 | Korthoff et al. |
| 4,610,383 A | 9/1986 | Rothfuss et al. |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| D294,518 S | 3/1988 | Green et al. |
| 4,881,544 A | 11/1989 | Green et al. |
| 4,915,100 A | 4/1990 | Green |
| 4,917,114 A | 4/1990 | Green et al. |
| 5,071,052 A | 12/1991 | Rodak et al. |
| 5,116,349 A | 5/1992 | Aranyi |
| 5,137,198 A | 8/1992 | Nobis et al. |
| 5,190,203 A | 3/1993 | Rodak |
| D338,729 S | 8/1993 | Spreckelmeier et al. |
| 5,240,163 A | 8/1993 | Stein et al. |
| 5,332,142 A | 7/1994 | Robinson et al. |
| 5,360,154 A * | 11/1994 | Green ..................... 227/179.1 |
| 5,395,030 A | 3/1995 | Kuramoto et al. |
| D357,981 S | 5/1995 | Green et al. |
| 5,445,644 A * | 8/1995 | Pietrafitta et al. ........... 606/151 |
| 5,465,895 A | 11/1995 | Knodel et al. |
| 5,470,010 A | 11/1995 | Rothfuss et al. |
| 5,505,363 A | 4/1996 | Green et al. |
| 5,553,765 A | 9/1996 | Knodel et al. |
| 5,597,107 A | 1/1997 | Knodel et al. |
| 5,632,432 A | 5/1997 | Schulze et al. |
| 5,655,698 A | 8/1997 | Yoon |
| 5,692,668 A | 12/1997 | Schulze et al. |
| 5,758,814 A * | 6/1998 | Gallagher et al. ....... 623/23.72 |
| 5,839,639 A * | 11/1998 | Sauer et al. ............. 227/175.1 |
| 5,871,135 A | 2/1999 | Williamson, IV et al. |
| 6,083,241 A | 7/2000 | Longo et al. |
| 6,102,271 A | 8/2000 | Longo et al. |
| 6,119,913 A | 9/2000 | Adams et al. |
| 6,126,058 A | 10/2000 | Adams et al. |
| 6,126,594 A | 10/2000 | Bayer |
| 6,142,933 A | 11/2000 | Longo et al. |
| 6,179,195 B1 | 1/2001 | Adams et al. |
| 6,193,129 B1 * | 2/2001 | Bittner et al. ............ 227/180.1 |
| 6,241,140 B1 | 6/2001 | Adams et al. |
| 6,279,809 B1 * | 8/2001 | Nicolo ..................... 227/176.1 |
| 6,302,311 B1 | 10/2001 | Adams et al. |
| 6,343,731 B1 | 2/2002 | Adams et al. |
| 6,478,210 B2 | 11/2002 | Adams et al. |
| 6,544,271 B1 | 4/2003 | Adams et al. |
| 6,585,144 B2 | 7/2003 | Adams et al. |
| 6,601,749 B2 | 8/2003 | Sullivan et al. |
| 6,605,078 B2 | 8/2003 | Adams |
| 6,629,630 B2 | 10/2003 | Adams |
| 6,632,227 B2 | 10/2003 | Adams |
| 6,695,198 B2 | 2/2004 | Adams et al. |
| 6,763,993 B2 | 7/2004 | Bolduc et al. |
| 6,805,273 B2 | 10/2004 | Bilotti et al. |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,916,332 B2 | 7/2005 | Adams |
| 2001/0054636 A1 * | 12/2001 | Nicolo ..................... 227/175.1 |
| 2003/0019905 A1 | 1/2003 | Adams et al. |
| 2003/0178465 A1 | 9/2003 | Bilotti et al. |
| 2004/0004105 A1 * | 1/2004 | Jankowski ............... 227/176.1 |
| 2004/0222268 A1 | 11/2004 | Bilotti et al. |
| 2005/0145672 A1 | 7/2005 | Schwemberger et al. |
| 2006/0025786 A1 | 2/2006 | Heinrich et al. |

FOREIGN PATENT DOCUMENTS

WO    WO 2004/110285 A1    12/2004

OTHER PUBLICATIONS

Abstract of On-table colonic lavage: an alternative. Sitzler PJ, Stephenson BR, Nicholls RJ. J R Coll Surg Edinb. Aug. 1998;43(4):276-7.

Abstract of Local and systemic effects of intraoperative whole-colon washout with 5 per cent povidone-iodine. Basha G, Penninckx F, Mebis J, Filez L, Geboes K, Yap P. Br J Surg. Feb. 1999;86(2):219-26.

Abstract of One-stage procedure in the management of acute sigmoid volvulus. Sule AZ, Iya D, Obekpa PO, Ogbonna B, Momoh JT, Ugwu BT. J R Coll Surg Edinb. Jun. 1999:44(3):164-6.

Abstract of Long tube for obstructing left-sided colon cancer. Adachi Y, Okita K, Nozoe T, Iso Y, Yoh R, Matsumata T. Dig Surg. 1999;16(3):178-9.

Abstract of Prospective study of primary anastomosis without colonic lavage for patients with an obstructed left colon. Naraynsingh V, Rampaul R, Maharaj D, Kuruvilla T, Ramcharan K, Pouchet B. Br J Surg. Oct. 1999;86(10):1341-3.

Abstract of Primary vs. secondary anastomosis after sigmoid colon resection for perforated diverticulitis (Hinchey Stage III and IV): a prospective outcome and cost analysis. Schilling MK, Maurer CA, Kollmar O, Buchler MW. Dis Colon Rectum. May 2001;44(5):699-703; discussion 703-5.

Abstract of Role of resection and primary anastomosis of the left colon in the presence of peritonitis. Biondo S, Jaurrita E, Marti Rague J, Ramos E, Deiros M, Moreno P, Farran L. Br J Surg. Nov. 2000;87(11):1580-4.

Abstract of Intraoperative colonic lavage with primary anastomosis vs. Hartmann's procedure for perforated diverticular disease of the colon: a consective study. Regenet N, Tuech JJ, Pessaux P, Zani M, Rouge C, Hennekinne S, Ama JP.

Abstract of Effect of intraoperative nutritional solutions on perianastomotic colonic mucosa in experimental large bowel obstruction. Aguilar-Nascimento JE, Oliveira-Neto JP, Mathie RT, Williamson RC. Dig Dis Sci.1 Dec. 1997;42(12):2581-4.

Abstract of Intraoperative colonic irrigation in the management of left sided large bowel emergencies in Jos University Teaching Hospital, Nigeria Sule A, Obepka PO, Iya D, Ogbonna B, Momoh J. East Afr Med. J. Nov. 2000;77(11):613-7.

Abstract of One-stage resection and primary anastomosis following acute obstruction of the left colon for cancer. Chiappa A, Zbar A, Biella F, Staudacher C. Am Surg. 2000 Ju;66(7):619-22.

Abstract of Single stage primary anastomosis without colonic lavage for left sided colonic obstruction due to acute sigmoid volvulus: a prospective study of one hundred and ninety-seven cases. De U, Ghosh S. ANZ J Surg. Jun. 2003;73(6):390-2.

Procedure for Prolapse and Hemorrhoids, 2003 Ethicon Endo-Surgery, Inc.

* cited by examiner

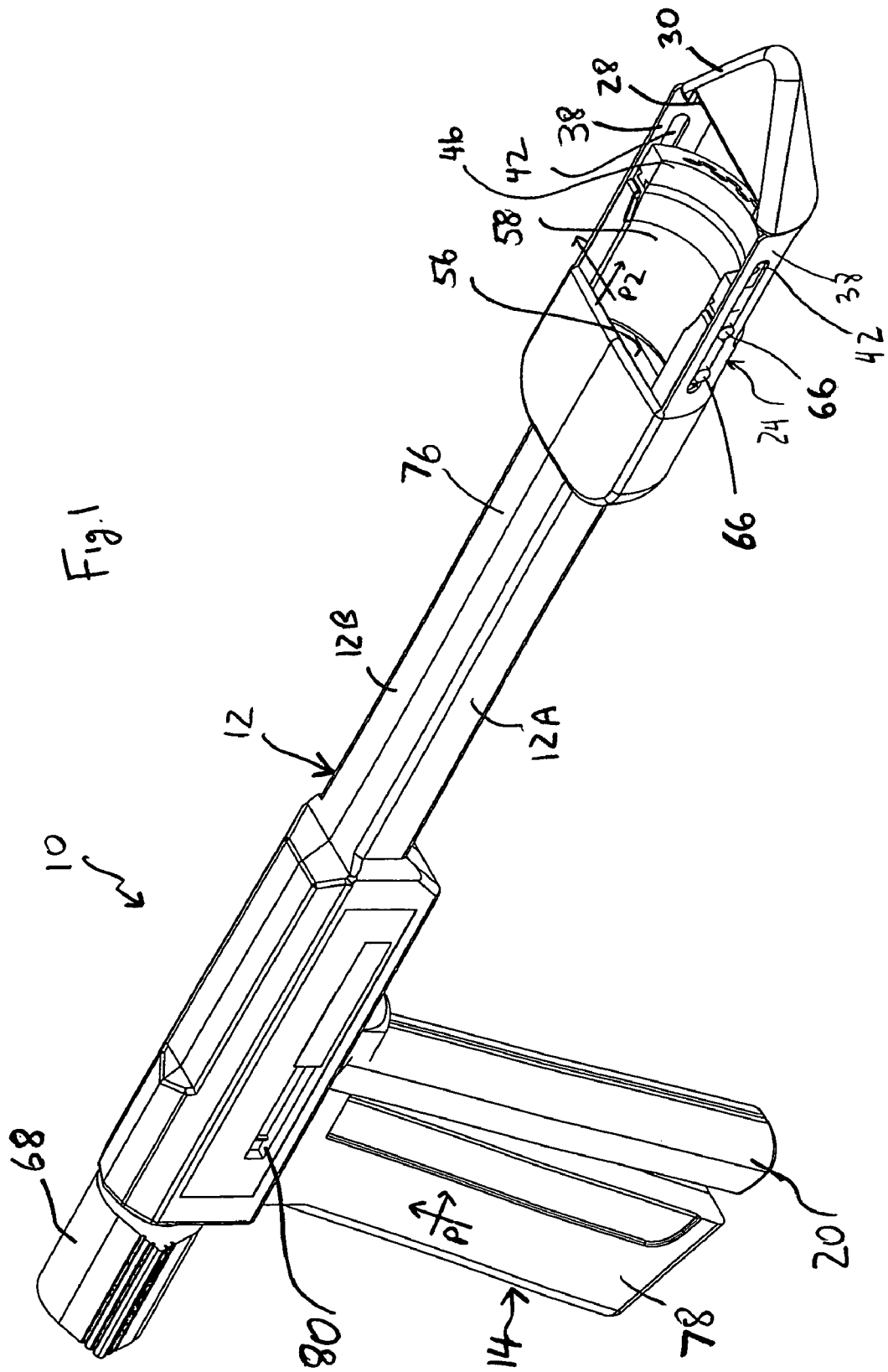

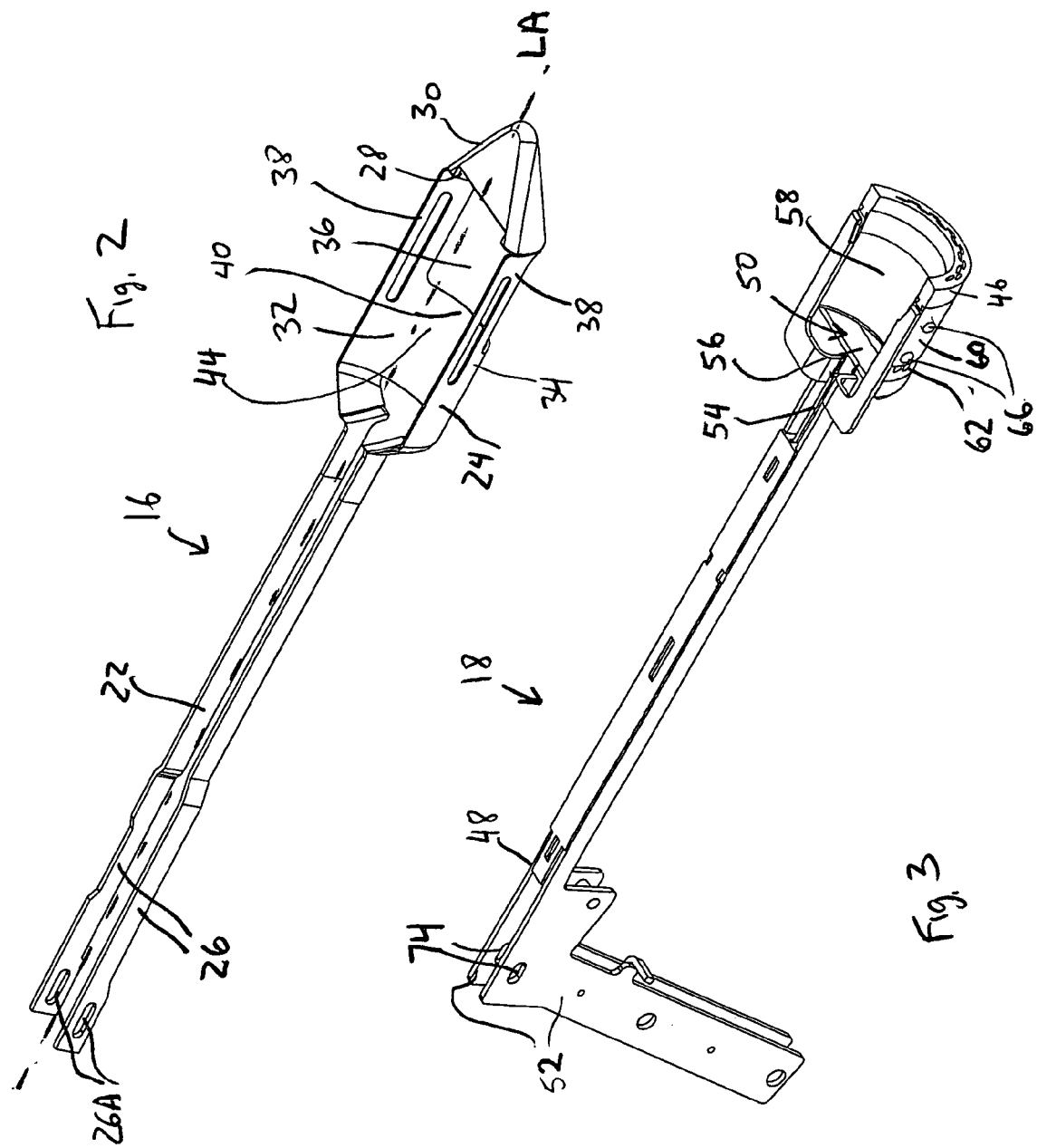

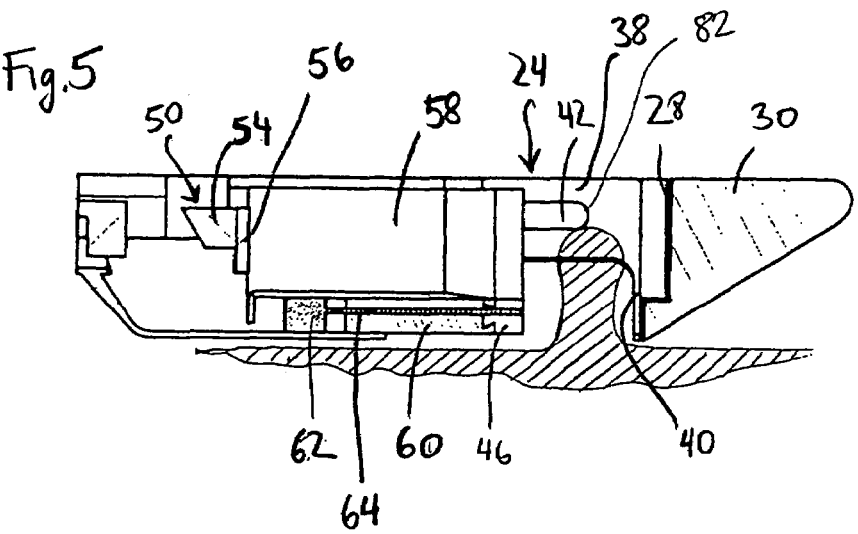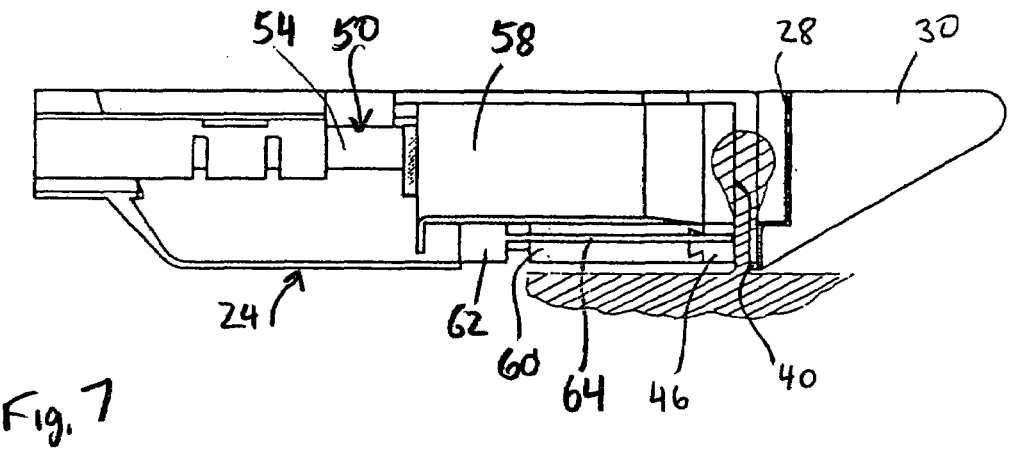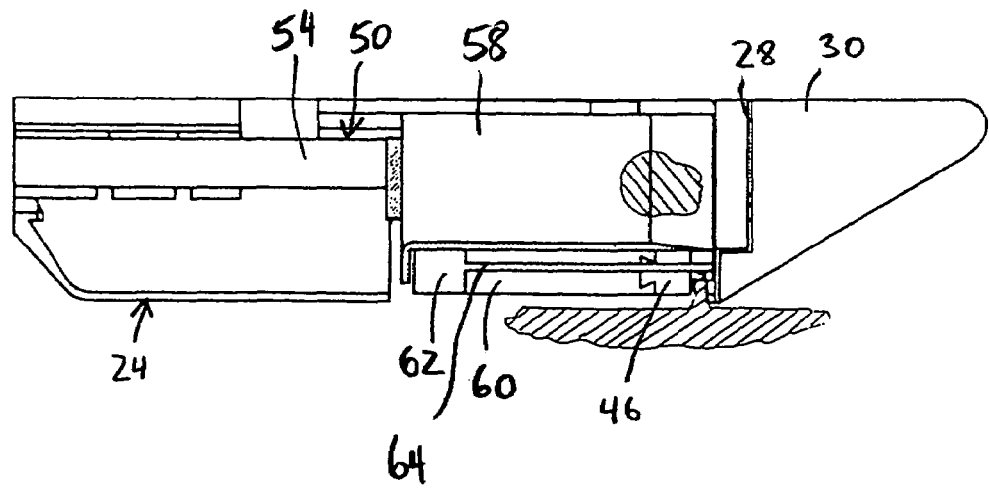

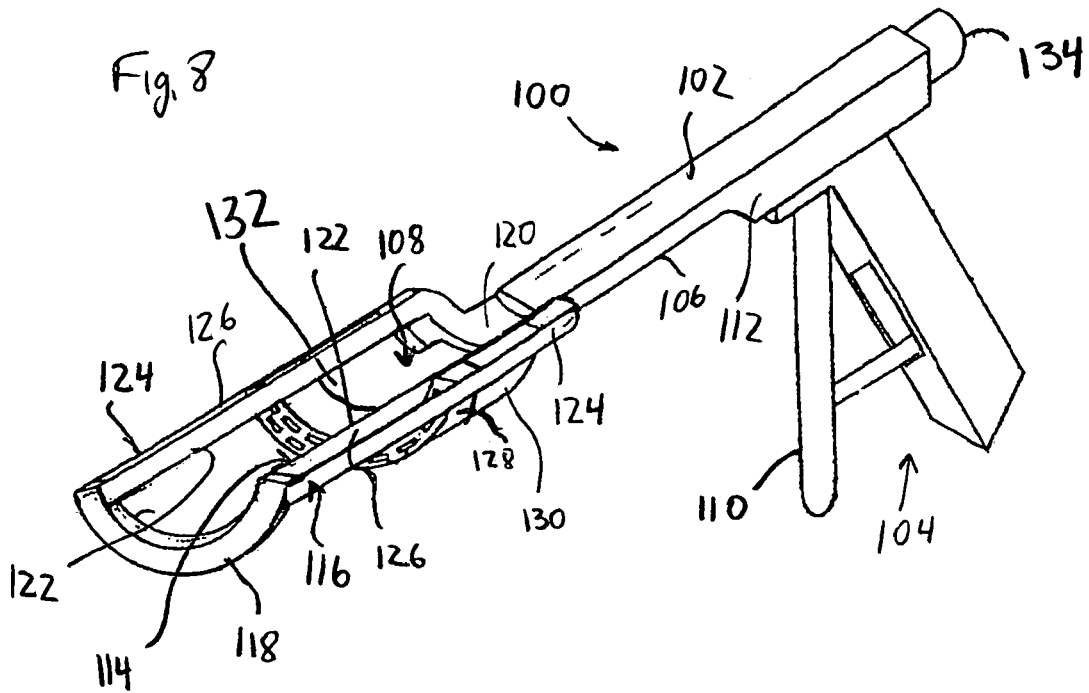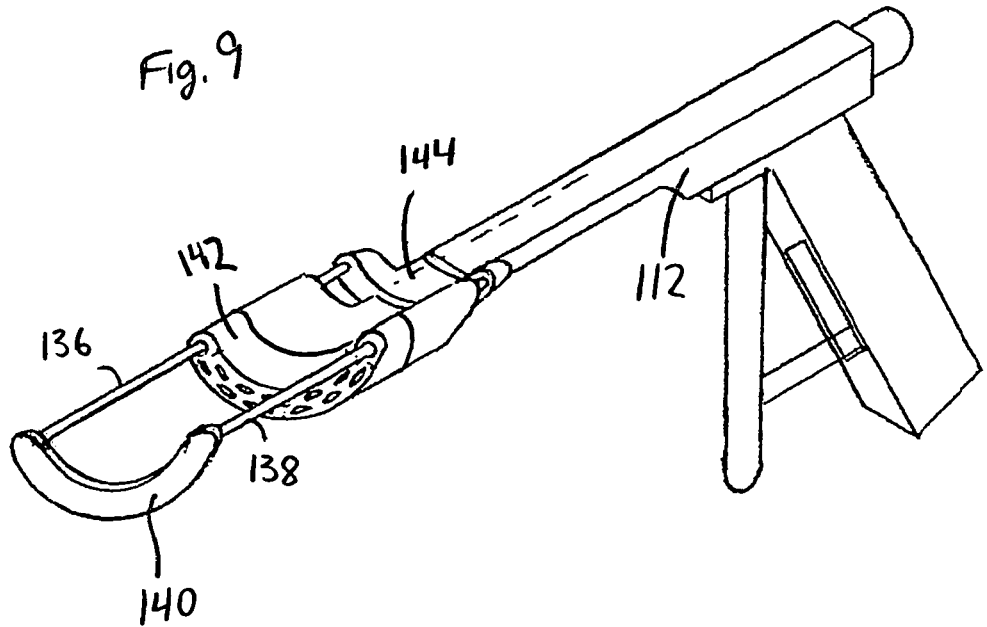

STAPLING APPARATUS HAVING A CURVED ANVIL AND DRIVER

CROSS REFERENCE TO RELATED APPLICATION

This application claims priority under 35 U.S.C. §119(e) of U.S. provisional patent application Ser. No. 60/592,548 filed Jul. 30, 2004, the specification of which is incorporated by reference herein.

FIELD OF THE INVENTION

The present invention relates generally to surgical staplers and more particularly to a surgical stapler which can excise a portion of the wall of a body cavity, and still more particularly to a surgical stapling instrument for the surgical treatment of hemorrhoids, mucosal prolapse of the anorectum, rectal polyps, rectoceles and obstructive defecation.

BACKGROUND OF THE INVENTION

Hemorrhoids are protrusions, bulges, folds, or irregularities of anal tissue, both inside the anal verge and outside on the anal margin. They are composed of epithelial lining (skin or mucus membrane), connective tissue and blood vessels in varying proportions. The dentate line, a distinct band normally located within the anal canal, marks the transition from columnar rectal mucosa to squamous anoderm. Hemorrhoids above the dentate line are referred to as "internal hemorrhoids", and hemorrhoids distal to the dentate line are called "external hemorrhoids". When internal hemorrhoids protrude beyond the anal verge, they are said to "prolapse". The entire circumference of the anus may be affected by hemorrhoids, or hemorrhoids may be restricted to one or two "quadrants" or sectors. Sometimes normal appearing lining of the upper anus and low rectum protrudes beyond the anal verge, a condition referred to as "mucosal prolapse."

Hemorrhoids are formed by the stress produced by bowel movements, straining and local irritation. Factors which contribute to the development of hemorrhoids may include aging, chronic constipation or diarrhea, pregnancy and heredity.

Hemorrhoids warrant treatment because of the symptoms they produce, including itching, bleeding, discharge, discomfort, and pain.

There are a number of known techniques used in the surgical treatment of hemorrhoids. These techniques include the excision or destruction of the hemorrhoidal tissue using scissors or scalpel, laser or infrared light, electricity or heat. Injection sclerotherapy is another treatment. Hemorrhoids may also be strangulated with ligatures, using small rubber rings ("rubber band ligation") or using sutures ("obliterative suture technique").

More recently, another procedure for the treatment of hemorrhoids has been developed whereby a circular stapler is used to remove a ring of anorectal tissue just above the hemorrhoids. This pulls the hemorrhoids back within the anus, flattens the hemorrhoids to some degree, and partially interrupts their blood supply, thereby rendering the hemorrhoids less symptomatic. This procedure is known as the "Procedure for Prolapse and Hemorrhoids (PPH)".

The instrument developed for use in the PPH operation consists of a modified circular endoluminal stapler, the stapler being sold under the name Proximate HCS™ (Hemorrhoidal Circular Stapler) by Ethicon Endo-Surgery, Inc. The instrument is described in U.S. Pat. No. 6,102,271, the method for its use is described in U.S. Pat. No. 6,083,241 and a special anoscope adapted to facilitate the performance of the procedure is described in U.S. Pat. No. 6,142,933. The disclosures of U.S. Pat. Nos. 6,102,271, 6,083,241 and 6,142,933 are hereby incorporated herein by reference.

The stapling instrument 25 disclosed in U.S. Pat. No. 6,102,271 (hereinafter "the '271 patent") conventionally includes a handle 30, a firing trigger 32 and an anvil closure knob 31 located at a proximal end of the device that is operatively coupled to an anvil assembly 60 such that the rotation of the knob 31 moves the anvil assembly 60 proximally or distally depending on the direction of rotation of the knob. Extending from the handle is a circular shaft 35 that is coupled at a distal end thereof to a circular stapling head assembly 41 for delivering a plurality of staples in a circular arrangement and simultaneously cutting the hemorrhoidal tissue upon actuation of the firing trigger 32.

The PPH operation using the stapling instrument described in the '271 patent is described in U.S. Pat. No. 6,083,241 (hereinafter "the '241 patent"). The procedure described in the '241 patent generally includes the following steps: a circular anal dilator 100 is inserted into the anus and the sheath of the anal dilator 100 is sutured to the perianal skin with silk sutures. Thereafter, an anoscope 120 is inserted within the anal dilator 100 and a purse-string suture 27 is sutured into the lining of the anorectum circumferentially at a location above the internal hemorrhoids. The anoscope 120 is removed and the open stapling instrument 25 is inserted into the anorectum. As the instrument 25 is inserted into the anorectum, the anvil assembly 60 passes through the pursed-stringed bowel. The surgeon then ties the purse-string drawing the anorectal lining around the shaft of the instrument 25 between the anvil assembly 60 and stapling head assembly 41. The surgeon then draws the ends of the tied purse-string suture through the barrel of the stapling head assembly 41, one on each side of the instrument 25. The ends of the purse-string are then tied together to form a loop. The surgeon closes the instrument 25 while maintaining tension on the loop of the purse-string suture 27, which helps draw the hemorrhoidal tissue inward into the barrel of the instrument 25. Closing the instrument 25 moves the anvil assembly 60 from the open position spaced from the stapling head assembly 41 to a closed position adjacent to the stapling head assembly 41 to clamp the hemorrhoidal tissue between the stapling head assembly 41 and the anvil assembly 60. The circular stapling instrument 25 is then fired to simultaneously cut and staple the hemorrhoidal tissue.

The PPH operation described above has some inherent shortcomings. First, the actions of forming the purse-string suture, tying the purse-string suture around the anvil shaft, and drawing the ends of the purse-string suture through the head of the stapling instrument are relatively difficult and manually intensive. Second, the surgeon must rely only on the purse-string and tension on the purse string to draw anorectal tissue into the instrument. Third, the surgeon cannot easily monitor the amount of hemorrhoidal tissue that is drawn into the stapling instrument because as the instrument closes his view is blocked by the stapling head assembly. Fourth, the amount of hemorrhoidal tissue excised is limited to the quantity of tissue that can be drawn into the barrel of the instrument. Fifth, the quantity of tissue drawn into the instrument and excised is inconsistent from case to case and is dependent upon multiple factors, including the skill with which the purse-string suture is placed, the level at which the purse-string suture is placed, the degree of prolapse, the disposition of hemorrhoids in the particular patient, the amount of anorectal inflammation present, the tension placed on the purse-string loop, and the orientation, or angulation of the stapler.

The amount, thickness and shape of the hemorrhoidal tissue can vary around the circumference of the rectum. However, since the stapling head assembly 41 and the anvil assembly 60 of the device disclosed in the '271 patent are rigid circular structures, the amount of hemorrhoidal tissue removed in a given sector of the rectum cannot be individually selected. This may result in inadequate treatment of the hemorrhoid in a given sector of the rectum. Likewise, when there is only a single hemorrhoid or a hemorrhoid is located in only one particular sector of the rectum, the device disclosed in the '271 patent cannot be easily used to treat only that hemorrhoid or that particular sector of the rectum.

Another problem with the PPH operation is that, often, after the stapler is fired, the staple line has a tendency to bleed requiring additional sutures for hemostatis which prolongs the procedure. Also, the staple line may dehisce, meaning that the staples may not hold the ends of the lining of the bowel together which can result in bleeding and/or infection. Further, in female patients, it is possible that the vaginal lining may be entrapped in the staple line. If the staple line then fails, a communication can then develop between the rectum and the vagina, a condition called rectovaginal fistula, which can result in the passage of flatus or stool through the vagina.

Another problem with the PPH procedure is that scarring can occur at the staple line causing the rectum to narrow which can result in a stenosis. If the staple line is placed too high in the rectum, an hour-glass configuration of the rectum could result, causing interference with the passage of stool.

Other stapling instruments adapted for use in transanal procedures are also known. For example, U.S. Pat. No. 6,302,311 (hereinafter "the '311 patent") describes a endoscopic stapler designed to achieve full thickness resection of a portion of the colonic wall. The endoscopic stapler 10 disclosed in the '311 patent includes a stapling head 12 and an attached sleeve 14 for feeding a conventional endoscope 16 therethrough. The stapling head 12 includes a stationary part 18 and a movable part 20. The endoscope 16 is fed through a portion of the sleeve 14 so that a distal end of the endoscope 16 resides in the stationary part 18 of the stapling head 12. The movable part 20 of the stapling head 12 includes a semi-circular anvil 48 and the stationary part 18 is adapted to fire a semi-circular double row of staples 32 and simultaneously cut the diseased tissue upon actuation of a control wire 22.

During use, the endoscopic stapler 10, together with the endoscope 16, are inserted into the anus, fed through the rectum and into the colon. A forceps instrument 26 is fed through a lumen in the endoscope 16 into the space between the stationary part 18 and the movable part 20 in order to enable the surgeon to pull tissue between the stationary part 18 and movable part 20. Once the tissue is arranged between the stationary part 18 and movable part 20, the movable part 20 is drawn towards the stationary part 18 by means of a control wire 24 until the tissue is grasped between the two parts 18 and 20. The control wire 22 is then used to fire the staples 32 from the stationary part 18 and simultaneously cut the tissue.

As noted above, the device disclosed in the '311 patent is primarily intended to be used to achieve full tissue resection of the colonic wall. Thus, the device is not specifically adapted to be used in hemorrhoidectomy procedures. Moreover, there are some structural features of the device disclosed in the '311 patent that make it ill-suited for such procedures. For example, as described above, in order to gain access to the tissue being removed, forceps 26 must be fed through a lumen in the endoscope 16. Thus, the surgeon does not have direct access to the tissue being treated making the procedure difficult. Moreover, in the device disclosed in the '311 patent, the movable part 20 and the stationary part 18 are interconnected by a central post 52, or three peripherally placed posts 352, 352 and 353, that would interfere with the surgeon's access to the bowel wall between the stationary part 18 and the movable part 20. Thus, when performing a hemorrhoidectomy, the posts would make it difficult to access the hemorrhoidal tissue and position the hemorrhoidal tissue between the stationary part 18 and movable part 20. Clearly, the embodiments shown in '311 patent are meant for use in conjunction with an endoscope, and are not designed to facilitate direct access to anorectal tissue.

Another use of the stapling instrument disclosed in the '271 patent is for the treatment of obstructive defecation. Obstructive defecation can be caused by the prolapse of the rectal lining within the rectum, rather than to the outside. Such prolapse can interfere with the passage of stool. The stapler disclosed in the '271 patent has been used in a procedure called Stapled Trans-Anal Rectal Resection (STARR) to remove a portion of the lining and thereby relieve obstructions. In this operation, the stapled of the '271 patent is used with a partial purse-string so that the mucosal lining of only a portion of the circumference of the rectum is captured within and removed by the instrument. However, such an effect could better be achieved by the invention disclosed herein as explained below.

U.S. Patent Publication No. 20040084505 shows a curved cutter stapler which, it is claimed, is useful for removal of tissue within the body cavity. The removal of rectal polyps, mucosal prolapse and rectoceles are potential uses sited in the patent. The use of this stapler for the specific treatment of hemorrhoids is not mentioned. However, this stapler has certain drawbacks. Since one longitudinal side of the stapling head is open, the opposite side must be strong enough, and therefore broad enough, to prevent movement of the anvil across its entire length, so that alignment will be maintained and staples properly formed. This makes the overall length of the stapling head large in comparison to the length of the staple line. As the angle of the arc increases, the more difficult it is for such a design to maintain alignment of the jaws upon closure of the instrument. As a result, the stapler becomes either unreliable, or unwieldy, and not suitable for use within the rectum. In addition, the handle of the stapler described in this patent publication is parallel to the plane of the middle of the arc of the stapling head, which makes it somewhat difficult to press against the wall of the rectum when holding the stapler by the handle alone. Furthermore, this stapler contains stapling lines on both sides of the blade. However, for use within the rectum to remove tissue from the wall, it would be preferable to have no staple lines only outside the curvature of the blade. In this situation it is not helpful to staple the tissue which will be removed, and doing so may make that tissue more difficult to remove. Stapling the tissue which is being removed would be particularly counterproductive if that tissue were a lesion which requires precise histologic examination.

OBJECTS AND SUMMARY OF THE INVENTION

It is therefore an object of the present invention to provide a new and improved surgical stapling instrument which avoids drawbacks of prior art surgical stapling instruments such as those mentioned above.

It is another object of the present invention to provide a new and improved stapling instrument that is specifically adapted for use in the surgical treatment of hemorrhoids and mucosal prolapse of the anorectum.

It is another object of the present invention to provide a new and improved stapling instrument that is specifically adapted for use in the surgical excision of rectal polyps or neoplasms. An instrument which can do this while closing the wound in a transverse direction would be particularly valuable because it would not narrow the lumen of the rectum.

It is another object of the present invention to provide new and improved stapling instruments that are specifically adapted for use in the surgical repair of rectocele and/or for use in the surgical treatment of obstructive defecation.

It is yet another object of the present invention to provide a new and improved surgical stapling instrument that provides ergonomic advantages over existing surgical stapling instruments for the removal of tissue from the anus and rectum.

It is still another object of the present invention to provide a new and improved surgical stapling instrument that is structured to optimize the application of force by a surgeon when resecting tissue from the wall of the anus or rectum.

It is yet another object of the present invention to provide a stapling instrument for the surgical treatment of hemorrhoids that permits the surgeon to directly and continuously view the hemorrhoidal tissue during the surgical procedure.

It is a further object of the present invention to provide a stapling instrument for the surgical treatment of hemorrhoids that allows the surgeon to have direct access to the hemorrhoidal tissue throughout the surgical procedure.

It is a further object of the present invention to provide a stapling instrument for the surgical treatment of hemorrhoids that allows the surgeon to more easily control the amount of hemorrhoidal tissue removed, to remove more tissue than can be removed using circular stapling instruments, and also allows the surgeon to remove tissue in only a selected sector of the rectum.

It is another object of the present invention to provide a stapling instrument for the surgical treatment of hemorrhoids that reduces the risk in female patients of the vaginal wall becoming entrapped in the staple line as compared to conventional stapling instruments.

It is still another object of the present invention to provide a stapling instrument for the surgical treatment of hemorrhoids that reduces the risks of the development of a post-operative stenosis of the rectum.

It is still another object of the present invention to provide a stapling instrument for the surgical treatment of hemorrhoids that promotes improved hemostasis.

Accordingly, the present invention is designed to excise or amputate mucosal and submucosal tissue from the inner wall of the anorectum and to simultaneously place an arcuate array of staples into the mucosal and submucosal layers of the anorectum beneath the amputated tissue, closing the defect created by the amputation. Whereas prior art stapling instruments used in the treatment of hemorrhoids remove an annular ring of anorectal tissue, the present invention removes hemorrhoidal tissue from a single sector at a time, each sector being less than 360 degrees, i.e., less than the entire circumference of the anorectum. However, like prior art circular stapling instruments, the staple line of this invention is oriented in the transverse direction, so that the rectal wall can be plicated transversely, thereby lifting the remaining hemorrhoidal or prolapsing mucosal tissue into a higher position in the anorectum where they become less prominent and symptomatic.

One embodiment of a stapling instrument in accordance with the invention generally comprises a body, a stapler head or actuating portion having a fixed jaw part connected to the body and including a non-linear anvil defining staple-forming pockets and two rigid, longitudinally extending struts as well as an actuating jaw part including a non-linear staple driver, a trigger coupled to the body for actuating the actuating jaw part, and a displacement mechanism for moving the actuating jaw part to vary a longitudinal dimension of an opening defined between the struts through which tissue is pulled to be amputated and stapled. The struts align at one end with spaced apart locations on the anvil and are coupled to the anvil to provide rigid longitudinal support therefor at two separate locations.

The staple driver has a plurality of tines adapted to align with staple blanks in a staple cartridge so that when the actuating jaw part is actuated by the trigger, it causes the tines of the staple driver to simultaneously force the staple blanks into the pockets of the anvil to thereby simultaneously form staples in tissue held in the opening between the fixed and actuating jaw parts.

When a non-linear cutting knife is associated with the actuating jaw part, actuation of the actuating jaw part causes tissue retained in a cavity communicating with the opening to be amputated substantially simultaneous with the formation of the staples in the tissue held between the fixed and actuating jaw parts.

The instrument preferably also includes a handle for the body which arranged in a plane which intersects a plane which constitutes a base of an arc of the staple driver and the anvil. Advantages of this orientation of the handle relative to the staple driver and anvil are described below. This orientation can be applied in stapling instruments with actuating portions different than those described immediately above.

Since the profile of the stapling instrument in accordance with the present invention is not circular, it allows the surgeon, with the aid of a retractor, to directly view and manipulate the anorectal tissue captured in the opening defined between the instrument's jaw parts. The size of the captured specimen can therefore be accurately controlled by the surgeon by controlling the amount of traction placed on the tissue. If desired, more tissue can be pulled through the opening defined between the jaw parts.

If a patient has hemorrhoidal disease or mucosal prolapse in one sector only, this invention can treat only that sector. On the other hand, if the patient's hemorrhoidal disease or mucosal prolapse is circumferential, then two or three applications of the instrument, or applications of two or three identical instruments, can remove more tissue in the aggregate than a circular stapling instrument can.

With this invention, it is not necessary to place a purse-string suture around the bowel wall, which can be a tedious task, and which can lead to unwanted bleeding or hematomas which can interfere with the performance of the procedure, or even lead to disruption of the staple line and postoperative bleeding and infection.

In females, the instrument can be oriented away from the anterior midline, making it much less likely to produce injury to the vagina.

If circumferential disease is treated with three firings of a single stapling instrument, or alternatively a single firing of each of three single-use stapling instruments, little tissue is removed in the sectors where the staple lines approach each other, making anorectal stenosis much less likely.

Previously, postoperative rectal bleeding has been a major problem with the Proximate HCS instrument. Placing a third concentric line of staples could solve that problem, but that would not leave enough room around the shaft of the anvil and within the barrel of the instrument for the anorectal tissue. Such a device would also more likely produce stenosis. However, adding a third parallel arcuate line of staples to the stapling instrument of this invention, would still allow the surgeon to draw ample tissue through the jaws. Also, when three quadrants are treated, stenosis would not be a problem because much less tissue would be removed where the ends of the staple lines approach each other. Hemostasis however would be superior with a third line of staples.

BRIEF DESCRIPTION OF THE DRAWINGS

The invention, together with further objects and advantages thereof, may best be understood by reference to the following description taken in conjunction with the accompanying drawings, wherein like reference numerals identify like elements, and wherein:

FIG. 1 is a perspective view of a first embodiment of an instrument in accordance with the invention in a pre-firing position.

FIG. 2 is a perspective view of a fixed jaw part of the instrument shown in FIG. 1.

FIG. 3 is a perspective view of an actuating jaw part of the instrument shown in FIG. 1.

FIG. 5 is a view showing tissue brought into the instrument in accordance with the invention.

FIG. 6 is a view showing the instrument in a closed position ready for the cutting and stapling.

FIG. 7 is a view showing the instrument after the tissue has been cut and stapled.

FIG. 8 is a perspective view of a second embodiment of an instrument in accordance with the invention.

FIG. 9 is a perspective view of a third embodiment of an instrument in accordance with the invention.

DETAILED DESCRIPTION OF THE INVENTION

Figure 4:
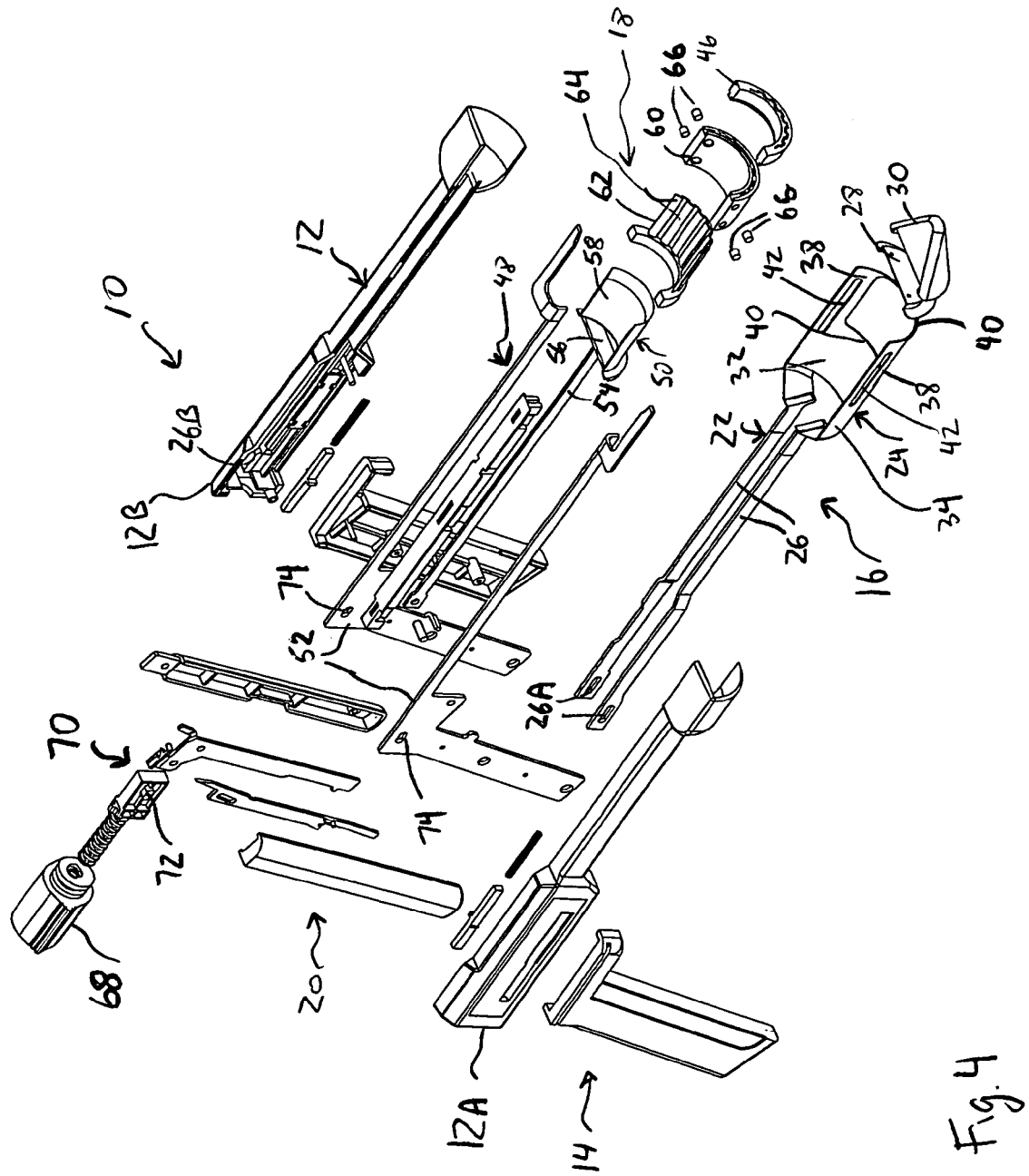
FIG. 4 is an exploded view of the instrument shown in FIG. 1.

The present invention is a novel surgical instrument particularly, but not exclusively, suited for the removal of tissue from a human patient. More particularly, the invention concerns the use of a stapling instrument for the removal of anorectal tissue to treat hemorrhoids, mucosal prolapse, polyps, rectocele and obstructive defecation.

Referring now to the drawings wherein like reference characters designate identical or corresponding parts throughout the several views, and more particularly to FIGS. 1–4, a stapling instrument in accordance with the present invention is designated generally by the reference numeral 10 and includes a rigid body 12, a handle 14 movable relative to the body 12 in a manner described below, an elongate fixed jaw part 16 fixed in position relative to the body 12 and an elongate actuating jaw part 18 arranged at least partially within and movable relative to the body 12 and fixed jaw part 16. A trigger 20 is attached to the handle 14 for actuating the actuating jaw part 18, and is also movable upon movement of the handle 14 relative to the body 12.

The fixed jaw part 16 includes a unitary, rigid main section 22 having a curved planar portion 24 and longitudinal extending shanks 26, an anvil 28 attached to an end of the main section 22 and a partial cone 30 attached to the anvil 28. Shanks 26 are attached to the body 12 in such a manner as to maintain the fixed jaw part 16 stationary upon movement of the actuating jaw part 18 caused by pressing the trigger 20 against the handle 14. For example, the shanks 26 may be provided with apertures 26A at a rear which receive lugs 26B formed on inner surfaces of body parts 12A, 12B (see FIG. 4).

Curved planar portion 24 curves about a longitudinal axis LA of the fixed jaw part 16 and has an inner curved surface 32, an outer curved surface 34 and an interior opening 36 extending through the curved planar portion 24 between the inner and outer curved surfaces 32, 34. As such, the opening 36 is delimited, surrounded or bound by the curved planar portion 24 on all sides except for on the inner and outer curved surfaces 32, 34, i.e., on the longitudinal and lateral sides of the opening.

By the curved planar portion 24 curving about the longitudinal axis LA, it is meant that cross-sections of the planar portion 24 in planes perpendicular to the longitudinal axis are substantially the same (at locations other than at the opening). Moreover, the curvature of the curved planar portion 24 is such that the axis about which the radius of curvature is defined is on the same side of the curved planar portion 24 as the longitudinal axis LA. Note though that the curved planar portion 24 does not necessarily have a constant radius of curvature.

To bind or delimit the opening 36, the curved planar section 24 of the fixed jaw part 16 includes a pair of opposed, substantially parallel, longitudinally extending struts 38 and a pair of opposed curved parts 40 each connected to respective longitudinal ends of the longitudinally extending struts 38 (see FIG. 2). Inner edges of the struts 38 and inner edges of the curved parts 40 define the opening 36 (the struts 38 defining lateral sides of the opening and the curved parts 40 defining longitudinal sides of the opening) and are substantially perpendicular to one another. Slots 42 are formed in the struts 38 to position and guide movement of the actuating jaw part 18 as described below.

As can be seen in FIG. 4, the curved parts 40 have a substantially semi-circular cross-section, and the curved planar portion 24 can be considered to generally have a semi-cylindrical form. However, this arcuate form is not limiting and the cross-section of the curved planar portion 24 and curved parts 40 thereof can be any other arcuate segment.

In view of the presence of portions of the fixed jaw part 16 around the opening 36 on its lateral and longitudinal sides, there is no access to the opening 36 from the lateral or longitudinal sides. Moreover, in view of the curvature of the curved parts 40, the main section 22 defines a cavity 44 radially inward from the inner curved surface 32 of the curved planar portion 24 which communicates with the opening 36.

Anvil 28 has a semi-circular, plate-like form and preferably includes two semi-circular rows, parallel to each other, containing staple-forming pockets that will mate with the staples in a staple cartridge 46 (see FIG. 3 discussed in detail below). Also, the anvil 28 may be provided with a cutting edge that mates with a cutting knife. The inclination provided by partial cone 30 enables easy penetration of the instrument 10 into the anorectum when the instrument 10 is used for hemorrhoidal surgery.

The construction of the curved planar portion 24 is designed to stably support the anvil 28 and ensure that staple blanks from the staple cartridge 46 pass into the staple-forming pockets in the anvil 28 in order to form staples upon firing of the instrument 10. In prior art rigid, linear stapling instruments, a single broad strut is typically provided to support the anvil and is quite wide to provide sufficient rigidity to the anvil. However, in the present invention, instead of a single strut, the curved planar portion 24 includes the two spaced apart, longitudinally extending struts 38 which, in combination, provide sufficient support for the anvil 28 while also providing an opening for grasping tissue being situated therebetween. The presence of two spaced apart struts for supporting an anvil at two separate locations in a curved, linear stapling instrument is an important feature of the invention and provides several advantages discussed elsewhere herein. By "curved, linear" stapling instrument, it is meant that one or more lines of staples are formed by the instrument and each line is curved.

Referring now in particular to FIG. 3, the actuating jaw part 18 has a support assembly 48 attached to the handle 14 and movable therewith and a driver member 50 movable relative to the support assembly 48 upon actuation of the trigger 20. Support assembly 48 includes rigid, elongate plates 52 partially extending into the handle 14. Driver member 50 includes a rigid driving shaft 54 situated between the plates 52, a transverse plate 56 attached to a forward end of the shaft 54 and oriented perpendicular thereto, and a curved cutting knife 58 attached to the transverse plate 56. Although the cutting knife 58 is shown as part of the driver member 50, i.e., the cutting knife 58 is integral with the transverse plate 56 as part of the driver member 50, it is envisioned that the cutting knife 58 can be formed as a separate member and removably attached to the transverse plate 56.

Actuating jaw part 18 also includes a casing 60 and a staple driver 62 having a plurality of tines 64 and arranged to pass through an interior of the casing 60. Casing 60 thus supports and guides movement of the tines 64 of the staple driver 62. The number of tines 64 on the stapler driver 62 correspond to the number of staples in the staple cartridge 46. Staple driver 62 is curved, with the tines 64 being spaced around the curvature thereof, and arranged radially outward from the cutting knife 58 (see FIG. 4). A rear surface of the staple driver 62 adjoins a forward surface of the transverse plate 56 of driver member 50. The combination of the casing 60, staple driver 62 and staple cartridge 46 can be considered a staple carrying unit.

Cutting knife 58 lies alongside the casing 60 and terminates at a straight forward edge so that it is capable of simultaneously cutting across its entire arcuate length. The straight forward edge can thus be substantially parallel to the surface of the anvil 28 against which the cutting knife 58 is forced.

Staple cartridge 46 is removably attached to the casing 60 and, as shown, includes two semi-circular rows of staple blanks parallel to each other and in a staggered arrangement (see FIG. 2). Surgical staple blanks measuring 4 mm by 4 mm may be used. In use, pulling the trigger 20 against handle 18 causes the driving shaft 54 to be forced forward relative to the fixed jaw part 16 thereby causing the cutting knife 58 and staple driver 62 to be forced forward toward the anvil 28. The tines 64 of the staple driver 62 simultaneously push the staple blanks in the staple cartridge 46 into the staple-forming pockets in the anvil 28 thereby causing the simultaneous formation of staples, i.e., the formation of two curved staple lines in the illustrated embodiment.

Actuating jaw part 18 is movable relative to the anvil 28 to adjust the longitudinal dimension of the opening 36 between the staple cartridge 46 and the anvil 28. This movement is guided by projections or pins 66 arranged on the casing 60 and extending through slots 42 (see FIG. 1). An adjustment knob 68 is arranged at the rearward end of body 12 and coupled to the plates 52 of the support assembly 48 via an adjustment bolt 70. For example, the adjustment bolt 70 may include lugs 72 which are received in slots 74 formed in the plates 52 (see FIG. 4). Rotation of the adjustment knob 68 causes longitudinal movement of the actuating jaw part 18, and handle 14 and trigger 20 connected thereto, relative to the fixed jaw part 16. As a result, rotation of the adjustment knob 68 causes the casing 60 (to which the staple cartridge 46 is attached) to move relative to the anvil 28 and thereby enable manual variation in the longitudinal dimension of the opening 36.

Appropriate structure for translating rotation of the adjustment knob 68 into longitudinal movement of the casing 60 and staple cartridge 46 attached thereto is shown in FIG. 4 and the manner in which this is effected would be readily apparent to one of ordinary skill in the art (see also U.S. Pat. No. 4,527,724, incorporated by reference herein, for additional details of this structure). Other mechanisms for guiding and causing movement of the casing 60 and staple cartridge 46 relative to the fixed jaw part 16 are also envisioned within the scope and spirit of the invention. In some embodiments, the casing 60 and staple cartridge 46 are part of an integral staple carrying unit including staple blanks and an actuatable mechanism for forcing the staple blanks forward into the pockets in the anvil, in which case, rotation of the adjustment knob 68 would translate into displacement of this staple carrying unit relative to the anvil 28.

In order to provide one or more arcuate staple lines, the cutting knife 58 and staple driver 62 are arcuate or curvilinear, and casing 60 can also be arcuate (or at least the pattern of channels therein through which the tines 64 pass to engage the staple blanks in the staple cartridge 46). The curvature and arc segment of these components is variable depending on the desired degree of arcuate coverage of the instrument 10, i.e., the length of the arcuate staple line(s).

Body parts 12A, 12B form a cover 76 which partially surrounds the fixed jaw part 16 and actuating jaw part 18. Structural details of the cover 76 and handle cover 78 are shown in FIG. 4. Additional details on this structure can be found in U.S. Pat. No. 4,527,724, incorporated by reference herein.

An important feature of the construction of handle 14 is that the handle 14 is oriented or arranged in a plane which intersects the plane which constitutes the base of an arc defined by the curved planar portion 24. Another way to consider this particular orientation of the handle 14 is that the plane of the handle 14 intersects the staple line being formed, the staple line being defined by the staple cartridge 46 or casing 60 when the staple cartridge 46 is not present or integral therewith. In the illustrated embodiment, the plane P1 of orientation of the handle 14 intersects the staple line and the plane P2, i.e., the plane which constitutes the base of the arc of the planar portion 24, at an approximate mid-point.

The construction of the handle 14 in this manner provides several important advantages. Notably, the handle 14 is located on the opposite side of the instrument 10 (relative to the curved planar portion 24) as cavity 44 into which tissue is pulled (as discussed below) and therefore does not block the surgeon's view of the surgical site, and the instrument 10 is easier for the surgeon to use. Another advantage is that since the handle part 14 is on a common side of the instrument 10 as the outer surface 34 of the curved planar portion 24, the surgeon is able to easily press the curved planar portion 24 down against the bowel wall and better position the stapler head to perform a hemorrhoidectomy.

Additional features are present in the instrument 10 which are generally common to surgical stapling instruments. For example, an indicator 80 is provided on the handle 14 to indicate the distance between the staple cartridge 46 and the anvil 28. Additional details on this structure can be found in U.S. Pat. No. 4,527,724, incorporated by reference herein.

A significant novelty of the stapling instrument 10 lies solely in construction of the actuating portion, i.e., the construction of the curved planar portion 24 of the fixed jaw part 16 and stapling and cutting components of the actuating jaw part 18. Indeed, this actuating portion alone is believed to be patentable. A stapling instrument in accordance with the invention can therefore include this actuating portion with any other necessary structure to enable its use, specifically any construction or combination of components which can move the driving shaft 54 of the actuating jaw part 18 forward relative to the fixed jaw part 16. For example, variations in the construction of the handle 14 and its parts, the trigger 20, the manner in which the trigger 20 causes movement of the driving shaft 54, the construction of the mechanism which adjusts the position of the casing 60 and staple cartridge 46 attached thereto relative to the anvil 28 including the adjustment knob 68, the indicator 80 are also possible and envisioned within the scope of the invention.

Fixed jaw part 16 and actuating jaw part 18 provide the body 12 with a pair of jaws which can be brought together to hold tissue therebetween and then allow the tissue to be amputated, e.g., by the cutting knife 58, and the tissue around the amputation to be stapled together, by the staples in the staple cartridge 46. In contrast to prior art linear staplers however, the tissue to be held between the jaws cannot be brought to a position between the jaws from a longitudinal side of the body 12. Rather, it must be brought into and through the opening 36. The formation of the opening 36, i.e., the construction of the curved planar portion 24 to provide the opening 36, and the manner in which the tissue is brought into the opening 36 are therefore novel features of the invention.

To use the instrument 10 for the removal of hemorrhoids, the instrument 10 is brought to a surgical environment in a pre-sterilized packaged condition and then removed from the sterilize package(s). The instrument 10 is packaged in a condition in which the actuating jaw part 18 is retracted from the fixed jaw part 16 the maximum distance, and preferably pre-loaded with a staple cartridge 46. In the case of replaceable staple cartridges, replacement cartridges would come wrapped separately and would be brought to the surgical environment along with the instrument 10.

Preparation of the patient involves positioning the patient in the prone-jack-knife or lithotomy position. An anal retractor is introduced. Next, the surgeon inserts a needle with suture thread 82 and passes the needle and thread through the anorectal tissue and then withdraws the needle. In this manner, the loop of thread 82 passes through the anorectal tissue and is held external of the patient. The thread may be passed through the hemorrhoid itself, in which case the hemorrhoid will be excised, or through the anorectal tissue slightly above the hemorrhoid, in which case, the hemorrhoid will be pulled back within the anus and flattened to some degree thereby rendering the hemorrhoid less symptomatic. Instead of using suture thread 82 to grasp the tissue, the tissue may be grasped directly with a grasping forceps.

The instrument 10 is then inserted into the anus taking care to ensure that the loop of thread is passed through the opening 36. While the loop of thread is slightly pulled, the instrument 10 is then positioned such that the prolapsed tissue passes through the opening 36 and is situated between the staple cartridge 46 and the anvil 28 (see FIG. 5).

The surgeon then turns the adjustment knob 68 to move the actuating jaw part 18, and the casing 60 thereof and staple cartridge 46 attached to the casing 60, forward toward the anvil 28 until the prolapsed tissue is pressed between the staple cartridge 46 and the anvil 28 (see FIG. 6). Ideally, the surgeon simultaneously maintains tension on the loop of the suture thread. Then, the surgeon fires the instrument 10 by pulling the trigger 20. This causes the driving shaft 54 and cutting knife 58 connected thereto to move forward with the cutting knife 58 amputating the prolapsed tissue while at the same time, the forward movement of the driving shaft 54 causes the tines 64 of the staple driver 62 to force the staple blanks in the staple cartridge 46 to pass through the edges of the remaining tissue into the pockets in the anvil 28 and thereby form staples which join the cut edges together (see FIG. 7). The forward or longitudinal movement of the cutting knife 58 causes whatever tissue is being impacted by the cutting knife 58 to be severed simultaneously from the remaining tissue.

Thereafter, the surgeon turns the adjustment knob 68 to cause the actuating jaw part 18 to retract enough to release its hold on the anorectal wall. The instrument 10 may be then be removed from the anus. The cut prolapsed tissue is still attached to the thread 82 and can be easily removed from the anus.

The volume of tissue captured between the staple cartridge 46 and the anvil 28, and therefore excised, can be easily adjusted by changing the tension on the apex of the parabolic volume of tissue. That is, if the surgeon wants to remove more tissue, he pulls harder on the loop thread 42 thereby pulling more tissue between the staple cartridge 46 and the anvil 28.

If the instrument 10 is designed for multiple uses with replaceable staple cartridges 46, the instrument can then be reloaded with another staple cartridge 46 and readied for further use for the same patient. In this case, another section of prolapsed tissue would be looped with thread 82 and the instrument 10 would be inserted with the loop of thread passing through the opening 36. The instrument 10 is then used in the same manner as described above. Since each firing of the instrument 10 is effective to cut prolapsed tissue from a 120° sector of the circumference of the anal mucosa membrane, the instrument can be used up to three times to encompass the entire circumference of the anal mucosa membrane.

In one embodiment of the invention, the instrument 10 is a single-fire instrument 10 in which a staple cartridge is formed as part of a staple casing. That is, instead of a separate casing 60 and staple cartridge 46 as described above, a single component is provided which includes an arcuate pattern of channels for passage of the tines 64 of the staple driver 62 therethrough and staple blanks arranged at the end of the channels. After firing the instrument 10, the entire instrument 10 is discarded and if additional stapling is needed, another instrument is readied for use.

A significant advantage of the invention over prior art hemorrhoidal staplers which resect along the entire circumference of the anal mucosa membrane is that for some patients, there is prolapsed tissue along only a portion of the circumference of the anal mucosa membrane. Thus, with the instrument 10, it is possible to resect only this prolapsed tissue without affecting the remaining tissue, e.g., when only one or two resections are performed with the instrument 10. This reduces stress on the anal mucosa membrane.

Another advantage is that the different resections with the instrument 10 in accordance with the invention can be slightly vertically offset from one another. This is particularly useful since the resection of each section of prolapsed tissue can be optimized.

Yet another advantage is that since the cavity 44 opens to a side of the instrument opposite the opening 36, it is possible to pull a significant amount of tissue through the opening 36, i.e., the instrument does not limit the amount of tissue that can be amputated.

In addition, the instrument 10 improves the surgeon's ability to perform the surgery since the cutting and stapling unit is semi-circular and therefore the surgeon can more easily view the surgical site than if the instrument was circular and blocked the surgeon's view of the surgical site. The surgeon can therefore easily monitor the amount of tissue that is captured between the staple cartridge 46 and the anvil 28 which will be removed. This reduces incidences in which an excessive or insufficient amount of tissue is removed.

In addition to its use for the removal of hemorrhoids, the instrument 10 in accordance with the invention can be used for any number of different surgical procedures requiring resection of tissue. For example, the instrument can be used in the treatment of mucosa prolapses of the rectum, rectoceles, rectal prolapses, rectal ulcers, Meckel's diverticulum, rectal stapling of trauma wounds, and transanal resection of rectal polyps or resection of colonic polyps via colotomies.

Various modifications to the instrument 10 described above are envisioned, some of which might be applicable depending on the intended use of the instrument. For example, the instrument 10 may be made in various sizes of staples and number of staples, this will depend in part on type of surgical use. To assure hemastosis, a third staple line can be provided in the staple cartridge, along with a third line of staple-forming pockets in the anvil. The third, or possibly any other additional staple lines would be situated outward of the cutting knife since there is no need for staple lines inward of the cutting knife as such staples would be needlessly stapling excised tissue.

Also, the cutting knife may be exchangeable and a safety latch can be provided to prevent premature firing of the instrument 10. The structure of the handle 14 can vary and includes any known or future type of handle which can be triggered to actuate a movable part containing a staple cartridge.

Furthermore, in another embodiment of the invention, the curved planar portion 24 can be formed without part or all of the curved part 38 at the edge adjacent the anvil 28. In this case, the anvil 28 itself serves to delimit the opening 36. Even in this case, in view of the formation of the opening 36 with structure on the longitudinal and lateral sides, it is not possible to operatively pass tissue into the opening 36 from the sides of the opening 36. Rather, the tissue must be brought to a position between the staple cartridge 46 and the anvil 28 in the manner described above.

Another embodiment of an instrument is shown in FIG. 8 and is designated generally as 100. The instrument 100 includes a body 102, a handle 104 movable relative to the body 102, a fixed jaw part 106 fixed in position relative to the body 102 and an actuating jaw part 108 arranged at least partially within and movable relative to the body 102 and fixed jaw part 106. A trigger 110 is attached to the handle 104 for actuating the actuating jaw part 108, and is also movable upon movement of the handle 104 relative to the body 102 and fixed jaw part 106.

The fixed jaw part 106 includes a housing 112, inner and outer strut members 114, 116 extending longitudinally from and fixed to one end of the housing 112, and a curved anvil 118 connected to the ends of the inner and outer strut members 114, 116. Housing 112 defines an interior space in which an actuating portion of the actuating jaw part 108 and the connecting structure between the actuating jaw part 108 and the trigger 110 are arranged. In view of the presence of housing 112 at one longitudinal end of the strut members 114, 116 and the anvil 118 at the opposite longitudinal end, an enclosed opening is formed by the fixed jaw part 106 which does not allow entry therein from the lateral or longitudinal sides.

The inner strut member 114 includes a central portion 120 adjacent to the housing 112 and a pair of inner struts 122 offset in opposite directions from the central portion 120. Similarly, the outer strut member 116 includes a central portion adjacent to the housing 112 and a pair of outer struts 124 offset in opposite directions from the central portion. Each outer strut 124 is spaced apart from a respective inner strut 122 to define a channel 126 therebetween.

The anvil 118 is connected to the ends of both the inner and outer struts 122, 124 and closes the channels 126 therebetween. Anvil 118 may have any curvature desired, e.g., a curvature of about 180°, and preferably includes two semi-circular rows, parallel to each other, containing staple-forming pockets that will mate with the 4 mm by 4 mm staples in the staple cartridge 128. Anvil 118 also preferably has a cutting edge that mates with a cutting knife. Optionally, a partial cone is attached to the anvil 118 to facilitate insertion of the instrument 100 into a body cavity.

Actuating jaw part 108 includes a curved staple driver 130 which is arranged with its lateral portions in the channels 126 between the inner and outer struts 122, 124. An optional cutting knife 132 is arranged in connection with the staple driver 130. Staple cartridge 128 is removably attached to the staple driver 130, radially outward from the cutting knife 132, by sliding the staple cartridge 128 through the channel 126 defined between one set of inner and outer struts 122, 124. As such, both the lateral portions of the staple driver 130 and the staple cartridge 128 will be positioned in the channels 126. Staple cartridge 128 may be formed as a unitary body with two semi-circular rows of staples parallel to each other with the staples being in a staggered arrangement. Surgical staples measuring 4 mm by 4 mm may be used.

If a single-fire instrument is made, the staple cartridge 128 and staple driver 130 can be formed as an integral unit.

The handle 104 is arranged in the same orientation relative to the curved staple line as described above, i.e., such that its plane intersects the plane which constitutes the base of an arc defined by the curved staple driver 130, to obtain the advantages mentioned above.

Actuating jaw assembly 108 can be actuated by trigger 110 as described above with respect to the actuation of actuating jaw part 18 by trigger 20. Actuation of actuating jaw assembly 108 shifts the cutting knife 132 and staple driver 130 forward to cause the cutting knife 130 to contact the cutting edge of the anvil 118 and the tines of the staple driver 130 to press staple blanks in the staple cartridge 128 into the staple-forming pockets of the anvil 118.

The space between the staple driver 130 and the anvil 118 may be adjusted in the same manner as the space between stapler driver 62 and anvil 28 is adjusted as described above, e.g., via an adjustment knob connected to the actuating jaw part.

Preparation and use of instrument 100 for the removal of hemorrhoids is substantially the same as described above for instrument 10 with the exception that the staple cartridge 128 is slid onto the staple driver 130 through the channel 126 between the inner and outer struts 122, 124.

This embodiment of the instrument 100 can be modified to eliminate the cutting knife 132 in which case, the instrument 100 would be used solely as a stapler and a separate cutting implement would be required if tissue is being amputated.

Essentially the same advantages described for the embodiment of the instrument 10 shown in FIGS. 1–4 are obtained for instrument 100 as well.

Another embodiment of the invention is shown in FIG. 9 which is similar to the embodiment shown in FIG. 8 except that strut members 136, 138 are cylindrical. The instrument may be designed with and without a replaceable staple cartridge. If the staple cartridge is replaceable, its lateral ends contain slots for receiving the strut members 136, 138 so that the cartridge may be removed from between the strut members 136, 138 and replaced.

Alternatively, anvil 140 is removably connected to the strut members 136, 138. By separating the anvil 140 from the struts 136, 138, it is possible to place a staple cartridge 142 onto the struts 136, 138. Alternatively, the struts 136, 138 can be removably mounted to a coupling member 144 of the housing 112 and the anvil 140 fixed to the struts 136, 138. In this case, the struts 136, 138 together with the anvil 140 are separated from the housing 112 so that the staple cartridge 142 can be mounted onto the struts 136, 138.

Staple cartridge 142 can include two or more lines of staples and an optional integrated cutting knife.

While basic embodiments of the present invention have been shown and described herein, it will be obvious to those skilled in the art that these embodiments are provided by way of example only. Numerous variations, changes, and substitutions will now occur to those skilled in the art without departing from the invention. For example, although reference is made in the description to a curved staple driver and curved cutting knife, any other non-linear form of these components can be used in the invention. Also, although in the embodiment shown in FIGS. 1–4, the handle and trigger connected thereto move relative to the body with the actuating jaw part upon rotation of the adjustment knob, it is envisioned that a surgical stapling instrument in accordance with the invention can have a handle and trigger connected thereto which do not move relative to the body. In one possible embodiment along these lines, the trigger can be designed to move the actuating jaw part and/or fixed jaw part to vary the longitudinal dimension of the opening defined between the staple cartridge and the anvil prior to firing of the staple driver. Alternatively, a separate non-firing trigger can be provided to move the actuating jaw part and/or fixed jaw part to vary the longitudinal dimension of the opening defined between the staple cartridge and the anvil. In addition, the use of the instrument described above with respect to FIGS. 5–7 is not limiting and other uses of the instrument to excise a portion of a membrane are envisioned and within the scope of the invention.

The invention claimed is:

1. An actuating portion of a surgical stapling instrument, comprising:
    a fixed jaw part including a non-linear anvil defining staple-forming pockets arranged in at least one row extending from one side of said anvil to an opposite side of said anvil, and a curved planar portion having a curved part and two rigid struts extending longitudinally from and being homogeneous with said curved part, each of said struts aligning with a respective one of sides of said anvil to thereby provide rigid longitudinal support for said anvil at two separate locations with said at least one row of staple-forming pockets of said anvil between said two locations, said struts defining an opening there between; and
    an actuating jaw part including a non-linear staple driver having a plurality of tines adapted to align with staple blanks in a staple cartridge,
    said actuating jaw part being arranged to actuate and cause said tines of said staple driver to force the staple blanks into said pockets of said anvil to thereby form staples in tissue retained in said opening.

2. The actuating portion of claim 1, wherein said actuating jaw part further comprises a nonlinear cutting knife arranged to amputate tissue retained in a cavity communicating with said opening substantially simultaneous with the formation of the staples in the tissue held between said fixed and actuating jaw parts.

3. The actuating portion of claim 2, wherein said cutting knife is arranged adjacent an inner surface of said actuating jaw part and said staple driver is arranged radially outward from said cutting knife such that staples are formed only radially outward relative to said cutting knife.

4. The actuating portion of claim 1, wherein said staple driver is movable longitudinally on, along or over said fixed jaw part.

5. The actuating portion of claim 1, wherein said staple driver is curved and said anvil has a arcuate form corresponding to the curvature of said staple driver.

6. A surgical stapling instrument, comprising:
    the actuating portion of claim 5;
    a body, said fixed jaw part being connected to said body and said actuating jaw part being movable relative to said body; and
    a handle for said body arranged in a plane which intersects a plane which constitutes a base of an arc of said staple driver and said anvil.

7. A surgical stapling instrument, comprising:
    the actuating portion of claim 5;
    a body, said fixed jaw part being connected to said body and said actuating jaw part being movable relative to said body; and
    a handle extending from said body in a direction which is the same as a direction of curvature of said anvil.

8. The actuating portion of claim 1, wherein said curved planar portion curves about a longitudinal axis of said fixed jaw part and has an inner curved surface and an outer curved surface, said opening extending through said planar portion from said inner curved surface to said outer curved surface and being bound by said curved planar portion on all sides except for on said inner and outer curved surfaces.

9. The actuating portion of claim 8, wherein said staple driver is curved and movable longitudinally on, along or over said curved planar portion of said fixed jaw part toward said anvil.

10. A surgical stapling instrument, comprising:
    the actuating portion of claim 1;
    a body, said fixed jaw part being connected to said body;
    a trigger coupled to said body for actuating said actuating jaw part; and
    displacement means for moving said actuating jaw part to vary a longitudinal dimension of said opening.

11. The actuating portion of claim 10, wherein said curved planar portion curves about a longitudinal axis of said fixed jaw part and has an inner curved surface and an outer curved surface, said opening extending through said planar portion from said inner curved surface to said outer curved surface and being bound by said curved planar portion on all sides except for on said inner and outer curved surfaces.

12. A surgical stapling instrument, comprising:
a body; an elongate, fixed jaw part connected to said body and including a curvilinear anvil defining staple-forming pockets; an actuating jaw part including an at least partially curvilinear staple carrying unit and movable toward said fixed jaw part; displacement means for moving said actuating jaw part toward said fixed jaw part; and a handle assembly including a handle and a trigger movable relative to said handle, said trigger being coupled to said body for actuating jaw part upon movement relative to said handle, said handle assembly being oriented in a first plane which is substantially perpendicular to a second plane tangential to an arc formed by a staple line defined by said staple carrying unit at the mid-point of the staple line,
said actuating jaw part being actuated by said trigger to cause said staple carrying unit to force staple blanks therein into said pockets of said anvil to thereby form staples in tissue retained in an opening defined by said fixed and actuating jaw parts.

13. The instrument of claim 12, wherein said fixed jaw part includes two rigid, longitudinally extending struts aligning at one end with spaced apart locations on said anvil and thereby providing rigid longitudinal support for said anvil at two separate locations, said struts defining said opening there between.

14. The instrument of claim 12, wherein said staple carrying unit includes a curved staple driver which is movable longitudinally on, along or over part of said fixed jaw part toward said anvil.

15. The instrument of claim 14, said actuating jaw part further comprises a curvilinear cutting knife arranged to amputate tissue retained in a cavity communicating with said opening substantially simultaneous with the formation of the staples in the tissue held between said fixed and actuating jaw parts.

16. The instrument of claim 15, wherein said cutting knife is arranged adjacent an inner surface of said actuating jaw part and said staple driver is arranged radially outward from said cutting knife such that staples are formed only radially outward relative to said cutting knife.

17. The instrument of claim 12, wherein said staple-forming pockets are arranged in at least one row extending from one side of said anvil to an opposite side of said anvil, said fixed jaw part including two rigid, longitudinally extending struts which provide rigid longitudinal support for said anvil at two separate locations with said at least one row of staple-forming pockets of said anvil between said two locations, said struts defining said opening there between.

18. The instrument of claim 12, wherein said trigger extends from said body in the same direction as said handle extends from said body.

19. An actuating portion of a surgical stapling instrument, comprising:
a fixed jaw part including a non-linear anvil defining staple-forming pockets and two rigid, longitudinally extending struts aligning at one end with spaced apart locations on said anvil and thereby providing rigid longitudinal support for said anvil at two separate locations, said struts defining an opening there between; and
an actuating jaw part including a non-linear staple driver having a plurality of tines adapted to align with staple blanks in a staple cartridge,
said actuating jaw part being arranged to actuate and cause said tines of said staple driver to force the staple blanks into said pockets of said anvil to thereby form staples in tissue retained in said opening, said actuating jaw part further comprising a non-linear cutting knife arranged to amputate tissue retained in a cavity communicating with said opening,
said cutting knife being arranged adjacent an inner surface of said actuating jaw part and said staple driver being arranged radially outward from said cutting knife such that staples are formed only radially outward relative to said cutting knife.

20. A surgical stapling instrument, comprising: a body;
an elongate, fixed jaw part connected to said body and including a curvilinear anvil defining staple forming pockets and defining an opening bound on lateral and longitudinal sides;
an actuating jaw part including an at least partially curvilinear staple carrying unit and movable longitudinally relative to said fixed jaw part alongside said opening;
a trigger coupled to said body for actuating said actuating jaw part;
displacement means for moving said actuating jaw part to vary a longitudinal dimension of said opening; and
a handle for said body arranged in a plane which intersects a plane which constitutes a base of an arc of said anvil and said staple carrying unit,
said actuating jaw part being actuated by said trigger to cause said staple carrying unit to force staple blanks therein into said pockets of said anvil to thereby form staples in tissue retained in said opening,
said staple carrying unit including a curved staple driver which is movable longitudinally on, along or over part of said fixed jaw part toward said anvil,
said actuating jaw part further comprising a curvilinear cutting knife arranged to amputate tissue retained in a cavity communicating with said opening,
said cutting knife being arranged adjacent an inner surface of said actuating jaw part and said staple driver being arranged radially outward from said cutting knife such that staples are formed only radially outward relative to said cutting knife.

* * * * *

UNITED STATES PATENT AND TRADEMARK OFFICE
CERTIFICATE OF CORRECTION

| | | |
|---|---|---|
| PATENT NO. | : 7,210,609 B2 | Page 1 of 1 |
| APPLICATION NO. | : 11/193600 | |
| DATED | : May 1, 2007 | |
| INVENTOR(S) | : Arnold R. Leiboff et al. | |

It is certified that error appears in the above-identified patent and that said Letters Patent is hereby corrected as shown below:

Cover page (56), OTHER PUBLICATIONS, column 2, change "irritation" to --irrigation--.

Column 16, line 6, insert --the-- after "of".

Column 16, line 10, change "there between" to --therebetween--.

Column 17, line 33, change "there between" to --therebetween--.

Column 17, line 56, change "there between" to --therebetween--.

Column 18, line 9, change "there between" to --therebetween--.

Signed and Sealed this

Twenty-sixth Day of June, 2007

JON W. DUDAS
*Director of the United States Patent and Trademark Office*